United States Patent
Ghavami-Nasr et al.

(10) Patent No.: US 9,296,549 B2
(45) Date of Patent: Mar. 29, 2016

(54) SPRAY DISCHARGE ASSEMBLY

(75) Inventors: Ghasem Ghavami-Nasr, Salford (GB); Andrew John Yule, Salford (GB); Martin Laurence Burby, Salford (GB)

(73) Assignee: THE SALFORD VALVE COMPANY LIMITED (GB)

( * ) Notice: Subject to any disclaimer, the term of this patent is extended or adjusted under 35 U.S.C. 154(b) by 493 days.

(21) Appl. No.: 12/948,110

(22) Filed: Nov. 17, 2010

(65) Prior Publication Data

US 2011/0186655 A1 Aug. 4, 2011

Related U.S. Application Data

(60) Provisional application No. 61/261,906, filed on Nov. 17, 2009.

(30) Foreign Application Priority Data

Apr. 13, 2010 (GB) .................................. 1006080.4

(51) Int. Cl.
| | |
|---|---|
| *B65D 83/28* | (2006.01) |
| *B65D 83/14* | (2006.01) |
| *B65D 83/20* | (2006.01) |
| *B65D 83/48* | (2006.01) |

(Continued)

(52) U.S. Cl.
CPC .............. *B65D 83/14* (2013.01); *B65D 83/207* (2013.01); *B65D 83/48* (2013.01); *A61L 9/14* (2013.01); *B05B 1/3442* (2013.01); *B65D 83/28* (2013.01)

(58) Field of Classification Search
CPC ......... F23D 14/04; F23D 14/10; F23D 11/10; B05B 1/28; B05B 1/18; B05B 1/265; B05B 1/267; B05B 1/3442; B65D 83/14; B65D 83/16; B65D 83/20; B65D 83/207; B65D 83/28; B65D 83/44; B65D 83/48; A61L 9/14
USPC .............. 239/419.5, 427, 499, 504, 518, 337
See application file for complete search history.

(56) References Cited

U.S. PATENT DOCUMENTS

| | | | | |
|---|---|---|---|---|
| 1,826,776 A | * | 10/1931 | Gunther | 239/8 |
| 3,545,492 A | * | 12/1970 | Scheid, Jr. | 138/42 |

(Continued)

FOREIGN PATENT DOCUMENTS

| | | |
|---|---|---|
| EP | 1 688 186 A2 | 8/2006 |
| EP | 1 754 540 A2 | 2/2007 |
| EP | 2 042 208 A1 | 4/2009 |

(Continued)

*Primary Examiner* — Christopher Kim
(74) *Attorney, Agent, or Firm* — Tarolli, Sundheim, Covell & Tummino LLP

(57) ABSTRACT

A spray discharge assembly is provided for use with an aerosol spray device comprising a pressurizable container holding a liquid to be discharged from the device by a propellant. The spray discharge assembly incorporates an approach channel having at least one inlet and an outlet, a flow conduit upstream of the approach channel in the direction of liquid discharge for supplying fluid to be discharged to the approach channel, at least one jetting orifice through which fluid from the conduit passes and issues as a jet into the approach channel through the inlet thereof, and a discharge orifice into which fluid from the approach channel passes via the outlet thereof to issue as a spray from the device. The outlet of the approach channel is surrounded by a sharp edge, and the jetting orifice is configured for directing the jet against the sharp edge.

19 Claims, 11 Drawing Sheets

Figure 1:
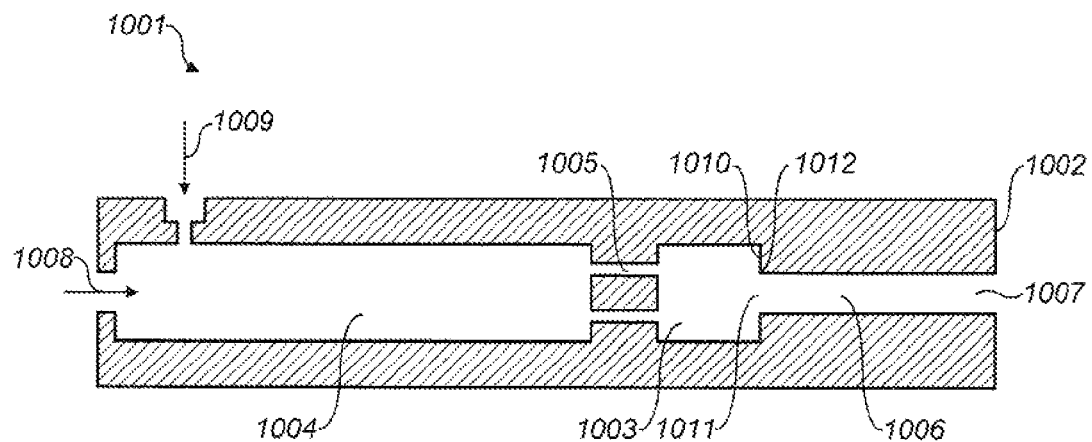

(51) Int. Cl.
  *A61L 9/14* (2006.01)
  *B05B 1/34* (2006.01)

(56) References Cited

U.S. PATENT DOCUMENTS

| 5,732,885 A | 3/1998 | Huffman |
| 2003/0082243 A1 | 5/2003 | Harman et al. |

FOREIGN PATENT DOCUMENTS

| WO | WO-90/05580 A1 | 5/1990 |
| WO | WO-90/05583 A1 | 5/1990 |
| WO | WO-03/062094 A1 | 7/2003 |
| WO | WO-2004/073879 A2 | 9/2004 |
| WO | WO-2006/122983 A1 | 11/2006 |

\* cited by examiner

SPRAY DISCHARGE ASSEMBLY

RELATED APPLICATION

This application claims priority from U.S. Provisional Patent Application No. 61/261,906, filed Nov. 17, 2009 and British Application No. GB 1006080.4, filed Apr. 13, 2010, the subject matter of which is incorporated herein by reference.

FIELD OF THE INVENTION

The present invention relates to a spray discharge assembly for use as an insert in an aerosol spray device for discharging a liquid product (e.g. a household product such as an air freshener) in the form of a spray. The invention has particular (but not exclusive) application to aerosol spray devices which utilise a compressed gas propellant rather than a liquefied gas propellant.

BACKGROUND TO INVENTION

Broadly speaking, aerosol spray devices comprise a container holding a liquid to be discharged together and an outlet nozzle associated with a valving arrangement which is selectively operable to allow discharge of the liquid as a spray from the nozzle by means of the propellant provided within the container.

Both "compressed gas propellant aerosols" and "liquefied gas propellant aerosols" are known. The former incorporate a propellant which is a gas at 25° C. and at a pressure of at least 50 bar (e.g. nitrogen, carbon dioxide or air). Such a gas does not liquefy in the aerosol spray device. On opening of the valving arrangement, the compressed gas "pushes" liquid in the spray device through the aforementioned nozzle that provides for atomisation. There are, in fact, two types of "compressed gas propellant aerosols". In one type, only liquid from the container ("pushed-out" by the compressed gas) is supplied to the outlet nozzle. In the other principal type, a portion of the propellant gas from the container is bled into the liquid being supplied to the nozzle which atomises the resulting two-phase, bubble-laden ("bubbly") flow to produce the spray. This latter format can produce finer sprays than the former.

In contrast, "liquefied gas propellant aerosols" use a propellant which is present (in the aerosol spray device) both in the gaseous and liquid phases and is miscible with the latter. The propellant may, for example, be butane, propane or a mixture thereof. On discharge, the gas phase propellant "propels" the liquid in container (including dissolved, liquid phase propellant through the nozzle).

It is well known that "liquefied gas propellant aerosols" are capable of producing finer sprays than "compressed gas propellant aerosols". This is due to the fact that, in the former, a large proportion of the liquefied gas "flash vaporises" during discharge of liquid from the aerosol spray device and this rapid expansion gives rise to a fine spray. Such fine sprays cannot generally be achieved with "compressed gas propellant aerosols", in either of the two principal formats described above.

Attempts have been made to improve the "fineness" of sprays generated by "compressed gas propellant aerosols". Prior art proposals have included the possibility of "bleeding off" some of the compressed gas (e.g. nitrogen) that is present in the container and mixing this with the liquid product to achieve "two fluid atomisation" which is a technique known to provide fine sprays for other areas of spray technology, e.g. liquid fuel combustion. However it has been found extremely difficult to produce fine sprays using two fluid atomisation with aerosol spray devices, and the nearest approach has been to use the equivalent of a vapour phase tap (VPTs are used in "liquefied gas propellant aerosols") to bleed some gas into the valve. However results for improving spray fineness have not been significantly beneficial.

It is therefore an object of the present invention to obviate or mitigate the above mentioned disadvantages.

SUMMARY OF THE INVENTION

According to a first aspect of the present invention there is provided a spray discharge assembly for an aerosol spray device comprising a pressurised or pressurisable container holding a liquid to be discharged from the device by a propellant, the spray discharge assembly adapted to be inserted in a fluid flow path between fluid in the container and a nozzle, the spray discharge assembly incorporating:

(i) an approach channel having at least one inlet and an outlet, (ii) a flow conduit upstream of said approach channel in the direction of liquid discharge from the nozzle for supplying fluid to be discharged to the approach channel, (iii) at least one jetting orifice through which fluid from the conduit passes and issues as a jet into the approach channel through the inlet thereof, and (iv) a discharge orifice into which fluid from the approach channel passes via the outlet thereof to issue as a spray from the device, wherein the outlet of the approach channel is surrounded by a sharp edge and the jetting orifice is configured for directing the jet against said edge.

Such spray discharge assemblies in accordance with the first aspect of the invention can be used as an insert within aerosol spray devices of either the "compressed gas propellant" type or the "liquefied gas propellant" type. Hence, in one embodiment, an assembly according to the first aspect of the invention is for an aerosol spray device comprising a pressurised container holding a liquid to be discharged from the device by a gaseous propellant that is a gas at a temperature of 25° C. and a pressure of at least 50 bar. In this embodiment, the flow conduit has inlets for liquid and gas obtained from the container so as to generate a bubble laden flow in the conduit, and wherein the flow conduit is configured for substantially disturbance free flow of said bubble laden flow to the jetting orifice.

According to a second aspect of the invention, there is provided an aerosol spray device comprising a pressurised or pressurisable container holding a liquid to be discharged by a propellant in the container, and a spray discharge assembly according to the first aspect of the invention. In one embodiment, the container may contain a liquefied gas propellant. In an alternative, preferred embodiment, where the container is pressurised, the container may hold a liquid to be discharged from the device by a gaseous propellant that is a gas at a temperature of 25° C. and a pressure of at least 50 bar.

Aerosol devices in accordance with the latter embodiment are "compressed gas propellant aerosols" and are able to generate fine sprays by virtue of the provision of the bubble laden flow (also referred to herein as a "bubbly flow"), the jetting orifice, the sharp edge and the discharge orifice. More particularly, in the aerosol spray device of the first aspect of the invention, a bubbly flow is created and is passed in a substantially disturbant-free manner to the jetting orifices. This can be achieved by configuring the flow conduit such that there is an absence of any flow disturbances, whereby the bubbly flow is delivered in substantially the form in which it was created to the upstream end of the jetting orifice. Additionally the valving arrangement present in the aerosol spray device should likewise not have any substantial effect on the bubbly flow once created. The jetting orifice produces a fine jet of fluid (liquid and gas, i.e. the bubbly flow) directed to the sharp edge at the outlet of the approach channel. At least a portion of the fluid strikes this edge before entering the discharge orifice. As a result of this interaction of the jets with the edge, there is flow separation from the wall of the discharge orifice in a relatively upstream region thereof and reattachment to the wall at a relative downstream region of the orifice. The separation and reattachment is a highly fluctuating phenomenon which, in combination with the bubbles in the fluid flow (which expand on being subjected to the pressure drop in the discharge orifice and cause liquid sheets between gas and liquid to break up and form a fine spray), is highly beneficial to the atomisation into droplets of liquid being discharged from the outlet of the discharge orifice.

The separation/reattachment effect is described in more detail below in relation to specific embodiments of the invention (see for example FIGS. 1 and 2 and related description). In order to achieve the separation and reattachment effect, it is necessary for the jetting orifice to direct fluid issuing therefrom to impinge on the sharp edge around the outlet of the approach channel. Separation and reattachment is achieved using a discharge orifice having appropriate cross-section and length dimensions. For example, for a circular section discharge orifice in an aerosol for which no swirl is imparted to the fluid being discharged, the discharge orifice will generally have a length to diameter (l:d) ratio of at least 4 although generally no more than 15. Typically the l:d ratio will be at least 5 more preferably at least 6. Different values may be appropriate for aerosol spray devices in which swirl is imparted to the fluid being discharged.

Preferably, there are a plurality of jetting orifices. There may, for example, be 3 to 6 such orifices although 4 is generally preferred. The jetting orifice(s) may be axially parallel to the approach channel or may be inclined to the axis of that channel to impart a degree of swirl to the fluid being discharged so as to increase the angle of the spray discharged from the device. Typically the degree of inclination for the jetting orifices will be up to 30° (e.g. up to 25°) with respect to the axis of the approach channel.

Preferably, the total cross-sectional area of the jetting orifices is greater than that of the discharge orifice.

The sharp angle around the outlet of the approach channel is provided by a reflex angle of at least about 270° (e.g. 270-330°), the value of 270°, itself being particularly preferred. Ideally the surfaces that converge together to form the edge do so without any "rounding" or "flattening" before the surfaces meet so the edge is not blunted. In other words they effectively converge to a "point" when seen in sectional view. However a degree of "rounding" or "flattening" may be tolerated. Although if there is any rounding it should not have a radius of more than 100 microns and is ideally less than 25 microns. In the case of "flattening", the width of any strip (as seen in sectional view) between the immediately adjacent regions of the two converging surfaces is preferably not greater than 50 microns and ideally less than 25 microns.

In accordance with some embodiments of the invention, gas from within the container is bled or otherwise introduced into the liquid flow being supplied along the flow conduit to the jetting orifice(s) so as to create a bubbly flow. In preferred embodiments, this flow conduit is of the same cross-sectional dimensions as the approach channel (both preferably being of circular cross-section). The conduit is configured so that liquid (e.g. fed along a dip tube) enters the upstream end of the conduit and gas is bled from the head space of the container into the liquid, ideally a short distance from the upstream end of the conduit. Typically the distance between the point at which gas is injected into the flow conduit and the outlet thereof (as provided by the entrance(s) to the jetting orifice(s) is 5 to 40 times the diameter of the conduit. The conduit may be linear and coaxial with the approach channel but this is not essential since it is envisaged that the conduit may curve towards the approach channel, provided that such curvature is not sufficient to modify the bubbly flow in the conduit significantly.

As described more fully below, embodiments of the invention allow production of a "bubbly flow" which is such that a flow of ideally homogenous bubbles, with similar diameter, and without stratification across the flow conduit passes into the jetting orifice(s) from which the bubbly flow then issues as turbulent bubble-laden jets which impact on the sharp edge (around the outlet of the approach channel) and enter the discharge orifice. The combination of the bubble laden jets and their impact on the sharp edge combine to give flow separation from the interior surface of the discharge orifice at an upstream region thereof with reattachment (at fluctuating locations) at a relatively downstream region. This results in a highly unsteady turbulent bubbly flow that is beneficial to the atomisation into droplets of the jet emerging from the outlet of the discharge orifice.

In certain embodiments of the invention, the spray discharge assembly may comprise a valve stem which is moveable between the first limit position in which the valving arrangement is closed so there is no discharge of liquid from the aerosol spray device and a second limit position in which there is such discharge. The valve stem may incorporate the flow conduit and have at least one liquid inlet (for providing liquid to the conduit) and at least one gas bleed inlet for bleeding gas from the headspace of the container into the conduit. The valving arrangement may comprise first and second spaced, fixed seals positioned such that in the first position of the valve stem the first seal closes the gas bleed inlet(s) and the second seal closes the liquid inlet(s). In the second position of the valve stem the gas bleed inlet(s) and liquid inlet(s) are moved away from their respective seals so that liquid is fed, and gas is bled into the conduit. Such an arrangement is such that there is essentially no modification of the bubbly flow when the valving arrangement is open.

In other embodiments of the invention (as applied to "compressed gas propellant aerosols"), the valving arrangement may comprise a "low loss" or "no loss" valve, i.e. one in which there is little or no pressure drop across the valve when open and fluid flows therethrough with the structure of the bubbly flow maintained. In all such cases, the low- or no-loss valve is effectively the "on/off" valve for the aerosol spray device and it is inserted in the conduit or between the conduit and the jetting orifices, so that liquid inlet(s) and gas bleed inlet(s) to the conduit (upstream of the "low loss" or "no loss" valve) may be left permanently open. The bubbly flow is generated upstream of the "low loss" or "no loss" valve, the latter being such that there is essentially no modification of the bubbly flow when the valve is open.

One example of valving arrangement incorporating a low loss valve suitable for use in the invention has a valve member with a bore of constant cross-section which is moveable between a first position in which the valving arrangement is closed and a second position in which the bore aligns with said upstream and downstream fluid flow path sections of the fluid flow path to provide for fully opening of the valving arrangement. In such embodiments, the aerosol spray device may comprise a fixed valve stem (in which the valve member is incorporated) and the valve member is moved between its closed and open positions by a mechanism (e.g. a linkage) operated by the actuator. The valve member may be rotatable between said first and second positions. Examples of valving arrangement of this type include ball valves and also cylinder valves in which the bore is transverse to the axis of rotation. A further example is a valving arrangement in which the valve member is cylindrical and the bore is axially parallel to, and offset from, the axis or rotation with which it is also parallel.

In a further embodiment of aerosol spray device incorporating a low loss valve, upstream and downstream sections of the fluid flow path are movable relatively towards each other with operation of the actuator mechanism to open the valving arrangement and said valving arrangement is opened by said relative movement to allow said upstream and downstream flow path sections to come into register with each other.

In this embodiment, the valving arrangement may, for example, incorporate a duckbill valve. Such a valve comprises two converging flaps of elastomeric materials which are biased together so as to maintain the valve closed. In the aerosol spray device, the duckbill valve is oriented so that these flaps converge towards the interior of the container and are held closed by the pressure therein. In order to open the duckbill valve (to effect discharge of fluid(s)) a tubular actuator (provided as part of the downstream fluid flow path section) through which fluid(s) may be flowed may be provided on an actuator cap of the spray device arranged such that, by depressing the cap, the lower end of the actuator engages against the interior surfaces of the converging flaps and causes them to open against the pressure of the gas within the container and allow the tubular actuator to come into register with the upstream flow path section whereby liquid may be discharged from the spray device.

In a further possibility for this embodiment, the valving arrangement may incorporate a flap having one end fixed in position and the other end in the form of a plug which removably locates in a lower end of the downstream flow path section, the device being such that on operation of the actuator mechanism to open the valving arrangement the plug is displaced from the lower end of the downstream flow path section which then comes into register with the upstream flow path section. The flap may, for example, be made of a resilient material.

A further example of valving arrangement incorporating a low loss valve that may be used in aerosol spray devices in accordance with the invention comprises a flexible walled tube connecting said upstream and downstream fluid flow path sections, tube closure means biased to a first position for pinching said tube to provide for the closed configuration of the valving arrangement, and tube opening means operable by the actuator to displace said tube closure means against the bias to provide for the open configuration of the valving arrangement.

Further disclosure relating to the use of low loss valves in aerosol spray devices is provided in our copending application (Application Ser. No. 61/261,912, filed on 17 Nov. 2009) entitled "Aerosol Spray Device", the disclosure of which is incorporated herein by reference.

As described above, a preferred embodiment of the invention relates to "compressed gas propellant aerosols" in which gas from the container is bled or otherwise introduced into the liquid to be discharged so as to create a "bubbly flow". The invention works with advantage in such aerosol formats. However, the principles described above are also applicable to other aerosol formats, such as in pressurised or pressurisable containers having other propellant types.

One embodiment of such an aerosol spray device is a "liquefied gas propellant aerosol" which may be constructed in accordance with the general principles outlined above for "compressed gas propellant aerosols", save that there is no requirement for bleeding gas into the liquid flow.

A further embodiment of aerosol spray device in accordance with the second aspect of the invention is a compressed gas aerosol in which only liquid is evacuated from the container. Such a device may be constructed in accordance with the general principles outlined above save that there is no requirement for bleeding gas into the liquid flow into the conduit.

Conveniently, aerosol spray devices in accordance with the invention may have an actuator cap formed with upper and lower recesses (chambers) which are coaxial with the approach channel and which are separated by a partition in which the jetting orifices are formed. In such arrangements, an insert is provided in the upper chamber and incorporates the discharge orifice as well as a portion of the approach channel which is completed by insertion of the insert into the recess so that the partitioning element forms the "back wall" of the approach channel. Conduit providing liquid flow to the jetting orifices may be located in the lower recess of the actuator cap.

BRIEF DESCRIPTION OF THE DRAWINGS

The invention will be further described by way of example only with reference to the accompanying drawings, in which:

FIG. 1 is a general schematic view of a spray discharge assembly according to a first aspect of the invention, for use in an aerosol spray device in accordance with a second aspect of the invention;

FIGS. 2*a* and 2*b* schematically illustrate operation of the spray discharge assembly shown in FIG. 1;

FIG. 3*a* schematically illustrates a first embodiment of aerosol spray device in accordance with the invention;

FIG. 3*b* shows a detail view of an alternative first embodiment;

FIG. 4 shows a detail of a spray discharge assembly (insert) incorporated in the spray device of FIG. 3;

FIGS. 5-7 illustrate modified constructions of spray discharge assemblies (inserts);

FIG. 8 illustrates a second embodiment of an aerosol spray device in accordance with the invention;

FIG. 9 illustrates a third embodiment of an aerosol spray device in accordance with the invention; and FIG. 10 illustrates a fourth embodiment of an aerosol spray device in accordance with the invention;

FIG. 11 schematically illustrates an alternative, 'bi-valve,' valving arrangement; and FIG. 12 schematically illustrates a different alternative, 'single gasket', valving arrangement.

DETAILED DESCRIPTION

Reference is made firstly to FIG. 1 which schematically illustrates the principle employed in the invention for causing a liquid held in a pressurised aerosol container to be discharged as a fine spray.

FIG. 1 shows an outlet arrangement 1001 for an aerosol can (not shown in detail in FIG. 1). As illustrated in FIG. 1, the outlet arrangement 1001 is shown as a one-piece component. However this is purely for the purposes of simplicity and it will be appreciated (and as illustrated in the embodiments shown in FIG. 3 onwards) that outlet arrangement 1001 may be formed from individual components that assemble together to provide the same function as the one-piece outlet arrangement 1001.

Outlet arrangement 1001 is comprised of a body 1002 internally configured to define a cylindrical approach channel 1003 communicating with an elongate, cylindrical flow conduit 1004 via jetting orifices 1005 and having a discharge orifice 1006 from the outlet end of 1007 of which (the right hand end in FIG. 1) a spray is discharged on operation of the aerosol. Approach channel 1003, flow conduit 1004 and discharge orifice 1006 are coaxial with each other.

The upstream end of flow conduit 1004 (i.e. the left hand end as seen in FIG. 1) is formed with a liquid inlet 1008 through which liquid (from within the aerosol container) flows during discharge of the aerosol. As depicted, liquid inlet 1008 is coaxial with flow conduit 1004. Additionally provided for flow conduit 1004 at a region downstream of the liquid inlet 1008 (i.e. to the right thereof as seen in FIG. 1) is a gas bleed inlet 1009 through which gas is bled into the conduit 1004 during aerosol discharge. In contrast with inlet 1008 which is coaxial with flow conduit 1004, the inlet 1009 bleeds gas into conduit 1004 in a direction perpendicular to the axis thereof, although other gas inlet angles may be employed, e.g. injecting at an angle of 45° upstream into the liquid.

To facilitate understanding of the following description, FIG. 1 has been further annotated to identify the portions of the wall of approach channel 1003 opposed to the outlet (downstream) ends of jetting orifices 1005 by reference numeral 1010. Additionally, the outlet of the approach channel 1003 (which is also the inlet to the discharge orifice 1006) is designated by reference numeral 1011.

It should be noted for the purposes of the following description, that the transition from the wall 1010 (of approach channel 1003) into the discharge orifice 1006 (i.e. at the region of the outlet 1011 of the approach channel 1003) presents a reflex angle of 270° internally of the approach channel. This transition provides a sharp edge 1012 at the outlet 1011 of approach channel 1003.

The manner in which outlet arrangement 1001 serves to generate a spray on discharge of the aerosol spraying device (effected for example by depressing an actuator button—not shown) is schematically illustrated in FIG. 2*a*. During discharge, liquid from within the aerosol container is caused to flow through the inlet 1008 into the flow conduit 1004 with gas simultaneously being bled into the flow conduit 1004 (and therefore into the liquid flow) from a head space in the container via gas bleed inlet 1009.

The bleed of gas into the liquid creates, within flow conduit 4, a bubble laden ("bubbly flow") which due to the internal configuration of the outlet arrangement 1 is such that a flow of homogenous bubbles, with similar diameter, and without stratification across the flow conduit and through the jetting orifices 1005 from which the bubbly flow issues as turbulent bubble-laden jets which impact on the sharp edge 1012 and enter the discharge orifice 1006. This is also illustrated in FIG. 2(*b*) from which it will be noted that the jets issuing from jetting orifices 1005 spread out at an angle (e.g. at least 20)°. This means that for the jets to impact on the sharp edge 1012 at the outlet to the approach channel 1003, the jetting orifices can be offset away from the centre line rather more than might be expected by simply protecting the jetting orifices into the discharge orifice.

The combination of the bubble laden jets and their impact on the sharp edge 1012 combine to give flow separation from the interior surface of the discharge orifice 1006 over an upstream region thereof. The length of discharge orifice 1006 is such that the flow reattaches to the wall at a downstream region thereof. The separation and reattachment is a dynamic process with the gas bubble 1014 in the recirculation zone continually growing then bursting or moving downstream, so that a new bubble starts to form. This results in a highly unsteady turbulent bubbly flow that is very beneficial to the atomisation into droplets of the jet emerging from outlet 1007 of discharge orifice 1006.

It should also be noted that the jets from the jetting orifices 1005 also provide the following phenomena:

They produce localised high velocity at the inlet edge which increases the size of the separated flow region inside the discharge orifice 1006.

They increase the turbulence level of the bubbly flow which increases the unsteady separation and reattachment of the separation zone in the discharge orifice 1006.

They cause further break up of the bubbles.

It should also be noted, that in the outlet arrangement 1001 that the bubbly flow does not pass through devices (such as conventional aerosol valves) that would cause the bubbles to merge or gas to stratify.

The following criteria may be adopted for ensuring operation of the outlet arrangement 1001 in the manner described.

The approach channel 1003 may have a diameter of 0.5-3 mm and a length of 0.5-2 mm. The diameter and the length may be the same in the range 0.5 to 2 mm and are preferably both about 1 mm.

Flow conduit 1004 may have a diameter from a half to twice that of approach channel 1003. The diameter of flow conduit 1004 which is preferably equal to that of approach channel 1003 may be from 0.5 to 2 mm, preferably, 0.75 to 1.25 mm. The length of flow conduit 1004 will be in the range of 5 to 40 times its diameter, more preferably in the range 5 to 15 times on the same basis. Ideally the length is 5 to 10 times the diameter on this basis.

With regard to jetting orifices 1005, there will generally be 2 to 10 such orifices each between 0.1 mm and 0.5 mm in diameter. These jetting orifices are preferably of equal diameter and/or equal spacing. The total cross sectional area of the jetting orifices should be between a value equal to that of the discharge orifice, and a value four times that of the discharge orifice. Generally the number of orifices will be in the range 3 to 6, with 4 being particularly preferred, each with a diameter of 0.25 mm.

Discharge orifice 1006 will typically have a diameter between 0.15 and 0.75 mm, more preferably between 0.25 and 0.5 mm. The length of discharge orifice 1006 is ideally from 4 to 12 times its diameter. Preferably discharge orifice 1006 has a diameter of 0.3 mm and a length 2 mm.

Gas bleed inlet(s) 1009 preferably have a diameter of from 0.1 to 0.5 mm, more preferably 0.15 mm to 0.25 mm. Typically there will be a maximum of two such inlets.

The following Table gives, by way of example, specific dimensions for an insert 1001 as illustrated in FIG. 1. These dimensions are particularly suitable for an insert 1001 to be used in an air freshener spray.

| Item | Reference Numeral | Diameter | Length |
|---|---|---|---|
| Approach channel AC | 1003 | 1 mm | 1 mm |
| Flow conduit | 1004 | 1 mm | 15 mm[1] |
| Jetting Orifices | 1005 | 0.25 mm | 0.5 mm |
| Discharge Orifice | 1006 | 0.3 mm | 2 mm |
| Gas Bleed Inlet(s) | 1009 | 0.15 mm | |
| Liquid Inlet | 1008 | 0.25 mm | |

[1]measured from the centre of gas inlet 1009 to the upstream end of jetting orifices 1005.

For the preferred embodiment detailed in the above Table, there are four jetting orifices 1005 each at an angle of 25° to the axial direction to give a degree of swirl. The centres of each orifice are on a circle of 0.5 mm diameter (Pitch Circle Diameter).

The bubbly flow should be at a velocity that gives a sufficiently short residence time of the flow in flow conduit 1004 such that bubble coalescence or stratification does not occur: Typically the flow should be in the range 0.5 to 5 m/s. For the preferred embodiment of aerosol spray device summarised in the above Table, the velocity is 1.0 m/s (equivalent to a flow rate of 0.8 ml/s through the 1.0 mm diameter approach channel. (It should however be noted that this is an approximate velocity that does not take into account that up to half the volume of the fluid in the flow conduit 1004 is taken up by the gas bubbles, so true liquid velocity is more like 2 m/s).

The bubbly approach flow should be at between 1 bar and 20 bar pressure, and in a preferred embodiment for a consumer aerosol can, between 4 bar and 12 bar (said pressure reducing during evacuation of the can for compressed gas aerosols. For the preferred embodiment of aerosol spray device detailed above, the initial pressure within the gas may be 12 bar which decreases to about 4.5 bar when all liquid in the pressurised container has been sprayed.

The ratio of volume of gas/volume of liquid contained in the bubbly flow in flow conduit 1004 should be between 0.2 and 4 at the pressure prevailing in this conduit and in a preferred embodiment for use with compressed gas aerosols, the ratio should be between 0.3 and 1.5. For the preferred embodiment outlined above, the volume ratio increases from about 0.35 when the pressurised container is fully charged with liquid to around 1.0 when the container is nearly empty.

The above pressures and volume ratios require that when the gas has expanded going through discharge orifice 1006, the ratio of volume of gas/volume of liquid in the emerging flow, is between 1.0 and 6.0, such a range of ratios being what is available from a compressed gas aerosol can in normal use.

The amount of gas bled through the inlet 1009 may be 4 to 8 times the liquid volume (using atmospheric conditions for these Figures). Higher Figures may cause the can pressure to reduce quickly and liquid to remain in the can when all can pressure has been depleted.

In the embodiment illustrated in FIG. 1, the jetting orifices 1005 extend parallel to the axes of approach channel 1003 and flow conduit 1004. However inclining the jetting orifices at a small angle (e.g. up to 30° with respect to the axial direction) can be used to increase the "cone angle" of the spray, i.e. the angle between the boundaries of the spray near the exit orifice. This "cone angle" will increase when the angle of inclination of the jetting orifices 1005 is increased but in an unpredictable way. Without inclination of the jetting orifices 1005, the "cone angle" may be around 20° whereas inclining the jetting orifices 1005 at an angle of 25° (as in the exemplary embodiment detailed above) gives a "cone angle" of around 30° and removes a tendency to a denser spray zone at the centre of the spray, especially at lower pressures.

The embodiment thus far described in relation to FIGS. 1 and 2 operates with gas being bled through the inlet 1009. It is however possible for the arrangement shown in FIGS. 1 and 2 to be modified so as to function without gas bleed, in which case the gas bleed inlets 1009 are omitted.

In this case, the jetting orifices deliver high speed liquid jets to the sharp edge of the inlet to the exit orifice;

i. This increases the likelihood of local regions of flow separation in the exit orifice;
ii. It also generates turbulence (good for giving atomization at the exit)

If the jetting orifices are given an angle (say 25-35 degrees) to the axial direction, the small amount of swirl is found to greatly improve atomization by causing the exiting turbulent liquid to disperse radially more rapidly giving a full cone spray. This is essentially different from the "swirl atomizer MBU" (Mechanical Break-up Unit) used in many consumer aerosols: these aim to give a thin conical liquid sheet which breaks up into drops.

Several specific embodiments of aerosol spray devices will now be described. In the following description, references to "upper" and "lower" are to the devices as illustrated in the drawings which are represented in their normal operational positions. In the description, the "rest" position is that in which the apparatus is not emitting a spray.

FIG. 3*a* illustrates a first embodiment of aerosol spray device 1 in accordance with the invention in the normal "rest" position. The device 1 comprises a pressurised container 2 on the top of which is mounted an aerosol valve assembly 3 which, as schematically illustrated in the drawings, is crimped on to the top portion of container 2. Provided within container 2 is a liquid to be dispensed from the device by a pressurised gas such as nitrogen, air or carbon dioxide which has limited solubility in the liquid 5 and is in a head space 6 of the container 2. The gas in the head space 6 may, for example, be at an initial pressure of 9 or 12 bar depending upon the type of container in use.

The valve assembly 3 comprises a generally cylindrical, axially movable valve stem 7 which at its lower end locates within a cylindrical housing 8 positioned internally of the container 2 and which at its upper end is fitted with an actuator in the form of a cap 9. This cap 9 is formed with upper and lower coaxial cylindrical recesses 10 and 11 respectively separated by a partition 12. Lower chamber 11 is of greater diameter than upper chamber 10 and serves to locate the cap 9 on the upper end of valve stem 7. Provided within upper chamber 10 a spray-generating insert 13 which will be described in more detail below.

In broad outline, the aerosol is operated by pressing down the cap 9 to cause downward movement of valve stem 7 with resultant discharge of a spray from insert 13, the spray being produced in the manner described more fully below.

As shown in the drawings, valve stem 7 is biased upwardly of the container 2 by means of a coil spring 14 locating at its upper end around a lower bulbous nose 15 on the valve stem 7. Lower end of coil spring 14 locates around an aperture 16 in lower wall 17 of the housing 8. Depending from wall 17 is a tubular spigot 18 fitted on lower wall enlarged end 19 thereof with a dip tube 20 which extends to the base of the container 2. It will be appreciated from the drawing, that the lower region of container 2 is in communication with the interior of the housing 8 via the dip tube 20, spigot 18 and aperture 16 (which provides a liquid inlet for housing 8).

For reasons which will become clear from the subsequent description, valve stem 7 has an external diameter slightly less than the internal diameter of housing 8 so that an annular clearance is defined between valve stem 7 and housing 8.

Annular gaskets 22 and 23 formed of rubber or other elastomeric material are provided at upper and central regions respectively of the housing 8 and are dimensioned to seal against the outer surface of valve stem 7. To facilitate understanding of the device as further described below, the aforementioned annular clearance is shown as being sub-divided into two sections referenced as 21*a* and 21*b*. Section 21*a* of the annular clearance extends between the two gaskets 22 and 23 whereas section 21*b* of the annular clearance is below gasket 23. Formed in the wall of the housing 8 between the two gaskets 22 and 23 are a plurality of ports 24 which provide for communication between the pressurised gas in the head space 6 and the annular clearance 21a.

Internally, valve stem 7 is formed with a flow conduit 25 and a liquid feed chamber 26 which extending coaxially along the valve stem 7. Flow conduit 25 extends from the upper end of valve stem 7 for over 50% of the length thereof. Chamber 26 is below flow conduit 25 and is of greater diameter than flow conduit 25 but significantly smaller length. Flow conduit 25 and chamber 26 communicate with each other via a coaxial passageway 27.

Figure 3A:
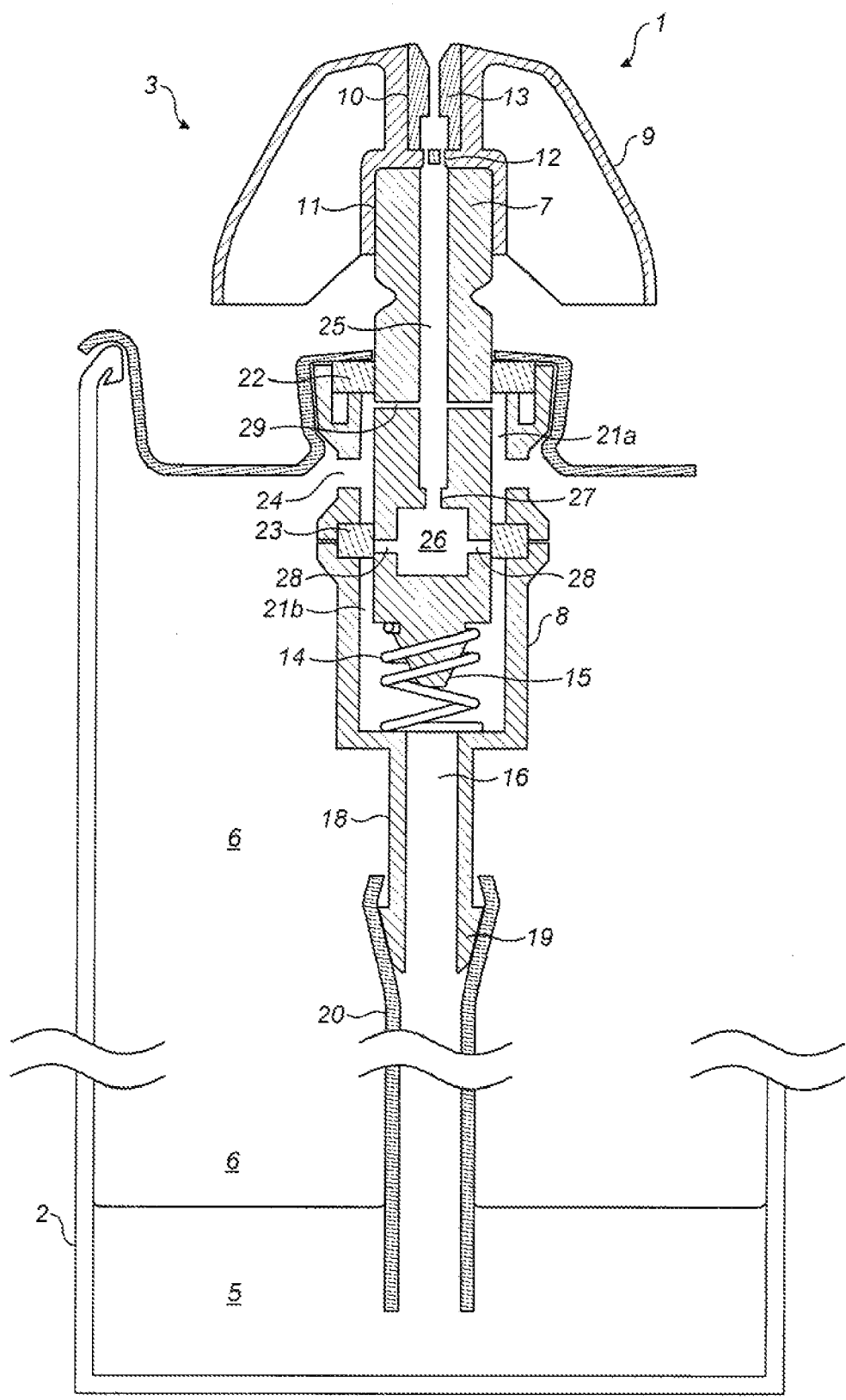
Figure 3B:
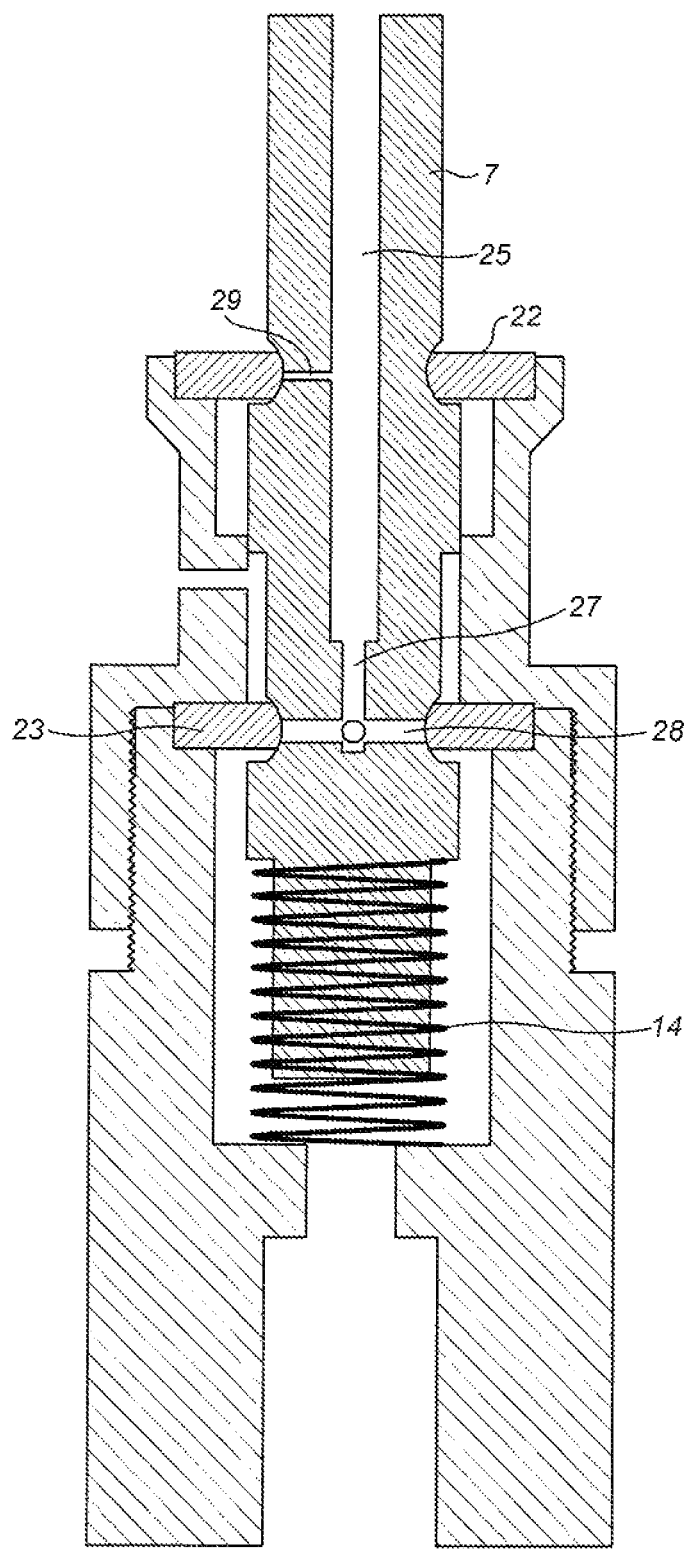

Two liquid feed passageways 28 extend transversely from the liquid feed chamber 26 and open at the outer surface of valve stem 7. Similarly, two gas bleed inlet passageways 29 extend transversely from the flow conduit 25 to open at the exterior surface of valve stem 7 (although constructions in which there is only one such inlet are also practical, one example of which is illustrated in FIG. 3b). In the "rest" condition of the aerosol shown in FIG. 1, the passageways 27 are sealed by upper gasket and passageways 28 are sealed by lower gasket 23. The cross-sections of the passageways 28 and 29 together with the axial spacing between these passageways and the dimensions of the upper and lower gaskets 22 and 23 are such that on depression of the valve stem 7 the gas bleed inlet passageways 29 are opened simultaneously with (or more preferably just before) the liquid feed passageways 28. The effect of opening the passageways 28 and 29 will be described more fully below.

As disclosed above, insert 13 is provided in the upper recess 10 of the actuator cap 9. Insert 13 is shown (to an enlarged scale) in FIG. 4 and comprises an approach channel 30 which is open at the lower end of the insert and a discharge orifice 31 which is of lesser diameter than approach channel 30 and which extends upwardly therefrom (and coaxially therewith) to open at the upper end of insert 13. It is to be noted that there are right-angled (sharp) edges 32 providing an abrupt transition between approach channel 30 and discharge orifice 31.

Formed within partition 12 are a number (e.g. four) of jetting orifices 33 which provide for communication between the flow conduit 25 (within valve stem 7) and the approach channel 30 of inlet 13.

Figure 4:
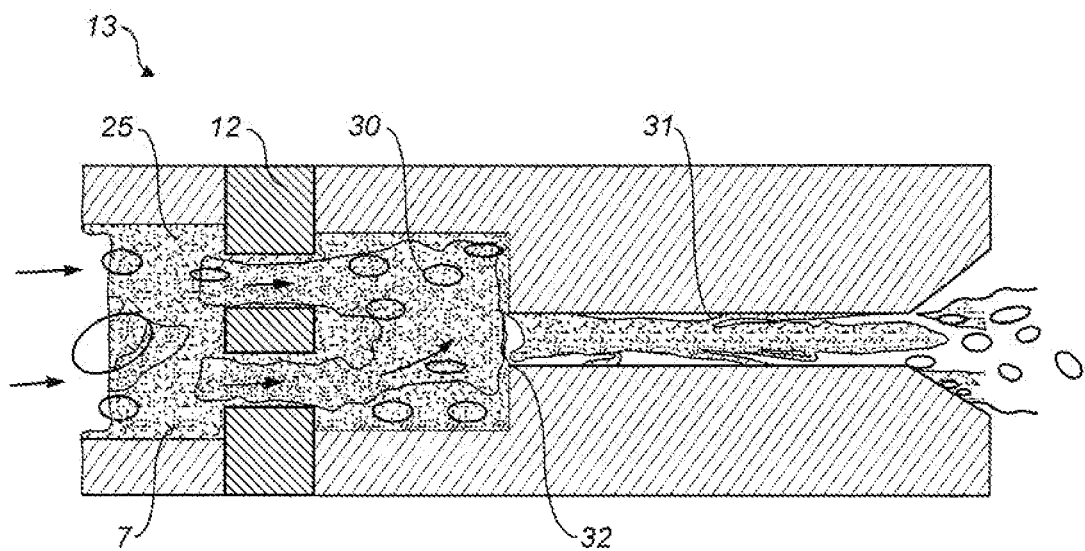

To facilitate understanding, the following table correlates certain component parts of the aerosol spray device of FIGS. 3 and 4 with the corresponding parts of the outlet arrangement 1001 illustrated in FIG. 1.

| COMPONENT PART | REF NO IN FIG. 1 | REF NO IN FIGS. 3 AND 4 |
| --- | --- | --- |
| Approach channel | 1003 | 30 |
| Flow conduit | 1004 | 25 |
| Jetting orifices | 1005 | 33 |
| Discharge orifice | 1006 | 31 |
| Liquid inlet | 1008 | 27 |
| Gas bleed inlet | 1009 | 29 |

It will be appreciated that component parts of FIG. 3 as identified in the table above may have the same dimensions as the corresponding component part in FIG. 1, these dimensions having been detailed more fully above.

Operation of the device illustrated in, and described above with reference to, FIGS. 3 and 4 is set out below.

Figure 2A:
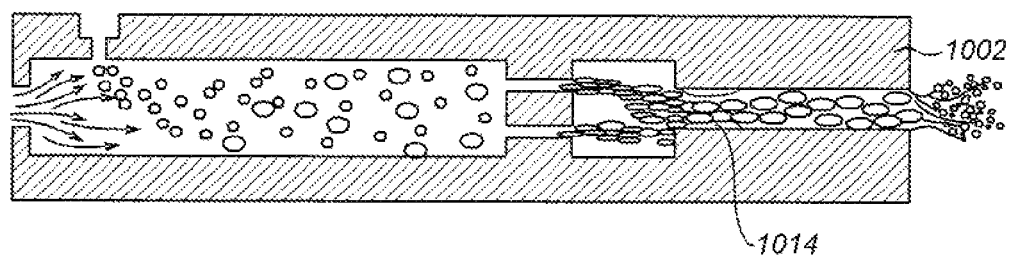
Figure 2B:
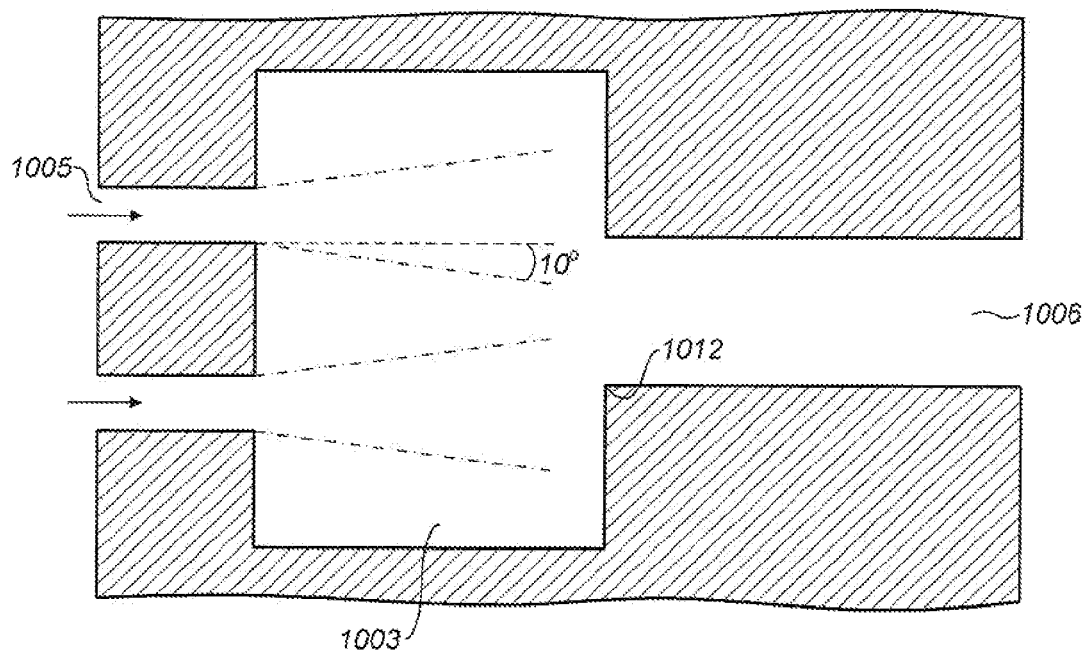

To operate the device 1, actuator cap 9 is depressed so that valve stem 7 moves downwardly against the bias of spring 14. As a result, gas bleed inlet passageways 29 are displaced from the gasket 22 such that compressed gas can bleed from head space 6 into the flow conduit 25 via the ports 24 (in the wall of housing 8), the annular clearance 21a and the gas bleed inlet passageways 29. Simultaneously with, or preferably slightly later than, the creation of the gas flow, one or more of the liquid inlet passageways 28 are opened by virtue of moving past lower gaskets 23. Liquid 5 can now flow into liquid feed chamber 26 by passage upwardly along the dip tube 20, through the inlet 16 into the housing 8, into annular clearance 21b and through the liquid inlet passageways 28. Liquid 6 introduced into liquid feed chamber 26 passes via passageway 27 into flow conduit 25 where it is mixed with compressed gas bled through the passageways 29. As a result, a flow of homogeneous bubbles with similar diameters and without coalescence or stratification is formed in flow conduit 25 and flows along the flow conduit 25 and through the jetting orifices 33 formed in the partition 12. These orifices 33 cause the production of jets of liquid and bubbles in approach channel 30 that are directed towards the sharp edges 32. As in the case of the outlet arrangement 1 described above in relation to FIGS. 1 and 2, the geometry of the insert 13 and the characteristics of the bubbly flow at the downstream end of the flow conduit 25 combine to give a number of turbulent bubble-laden jets impacting on the sharp edges 32, as depicted in FIG. 4 of the drawings. As a result of the production of these jets, fluid (liquid and gas) travels along the discharge orifice 31 in a manner such that there is flow separation from the wall of the first part of orifice 31. The length of orifice 31 is such that the flow re-attaches to the wall at a downstream region thereof. The separation and re-attachment is a highly fluctuating phenomenon which is very beneficial to the atomisation into droplets of the jet emerging from the exit of orifice 31. The result is a fine spray of liquid from the device. Furthermore, the fluctuations at the exit of passageway 30 provide a distinct hissing sound which is considered "attractive" to users of aerosols since such a sound is expected from current liquefied gas propellant aerosols.

Figure 5:
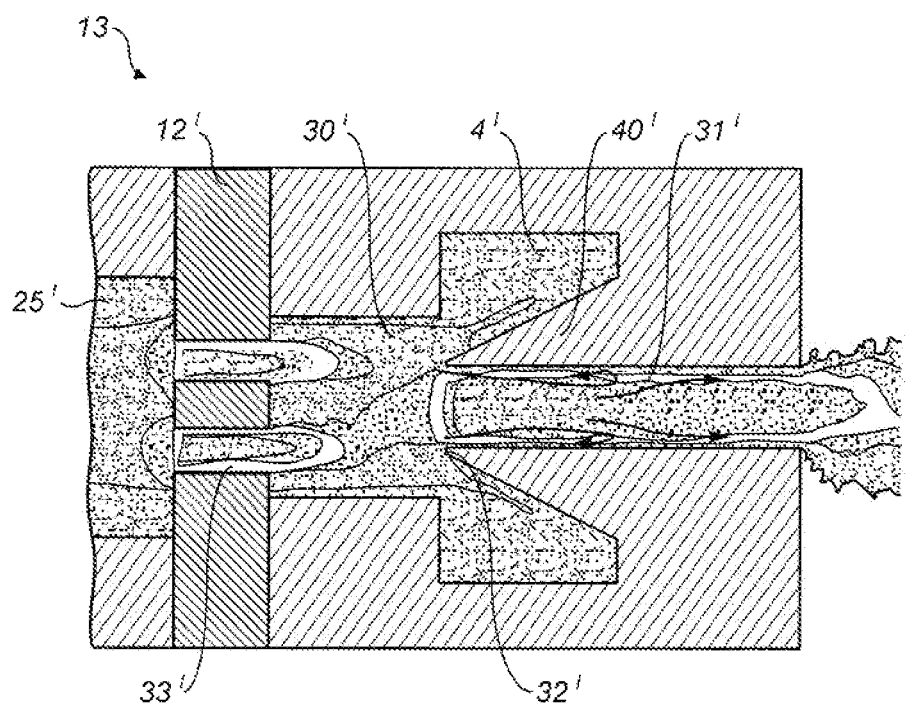
Figure 6:
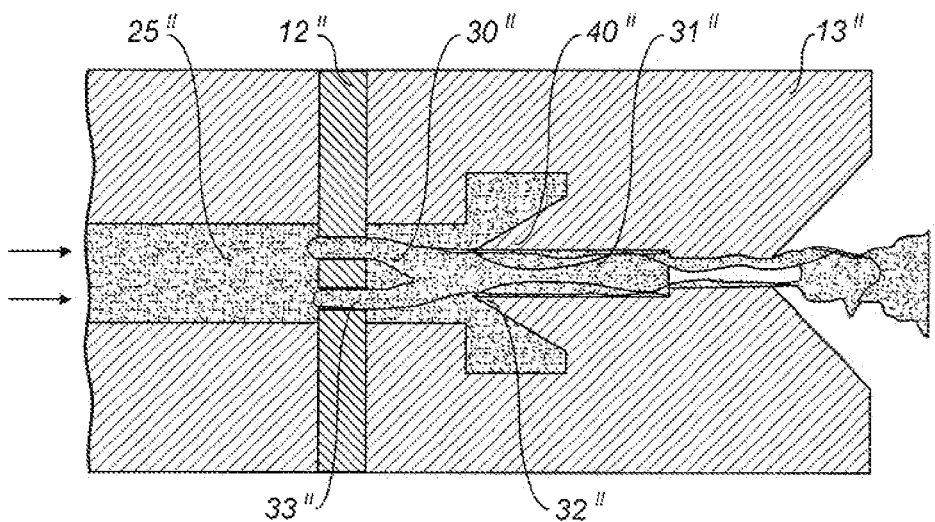
Figure 7:
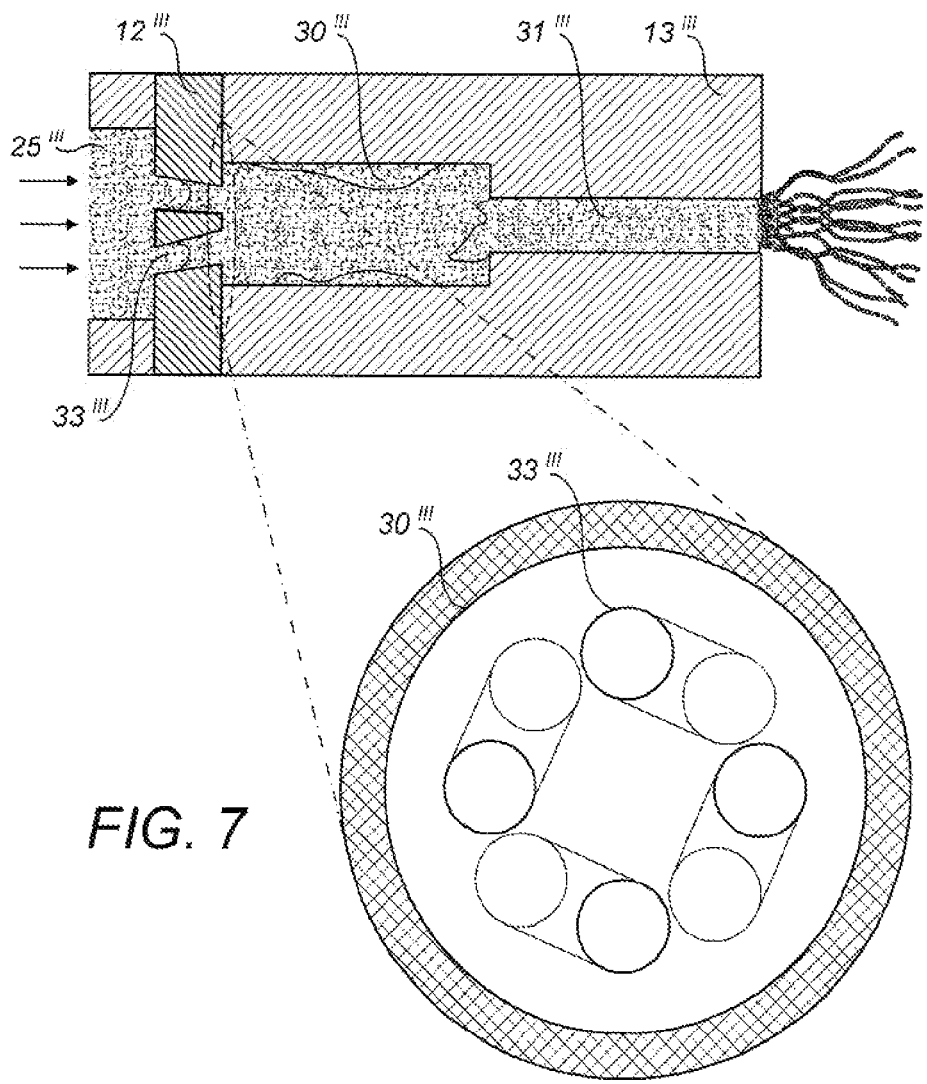

Reference is now made to FIGS. 5-7 which show modified versions of the insert 13 which also provide for separation and re-attachment in a highly fluctuating manner of the fluid flow along the discharge orifice 31. For convenience, parts in FIGS. 5-7 which are equivalent to those in FIG. 3a are designated by the same reference numeral but suffixed with one prime symbol (') in the case of the embodiment of FIG. 5, two prime symbols for the embodiment of FIG. 6, and three prime symbols for the embodiment of FIG. 7.

In the embodiment of FIG. 5, the right-angled edge 32 employed in the arrangement of FIG. 4 is replaced by a sharp edge 32' around the apex of a tubular, conical formation 40 which is surrounded by a recirculating chamber 41 in communication with approach channel 30'. As will be appreciated from FIG. 5, discharge orifice 31' extends over part of its length from the apex of conical formation 40. The sharp edge 32' assists in creating separation of the flow within the discharge orifice 31', thus enhancing spray generation.

The embodiment shown in FIG. 6 is similar to that of FIG. 5 save that the discharge orifice 31" abruptly reduces in diameter part-way along its length so that the orifice 31" has an upstream section (for convenience referred to herein as 31"u) of larger diameter than the downstream section (referred to for convenience as 31"d). By way of example the diameters of the upstream and downstream sections (31"u and 31"d respectively) may be either (i) 0.5 mm and 0.3 mm respectively, or (ii) 0.3 mm and 0.2 mm respectively.

Provided that the overall length of discharge orifice 31" is sufficient then the flow can separate and then re-attach in the upstream section 31"u of the orifice, which is beneficial for turbulence production, and then remain highly turbulent in the downstream section 31"d so as to give good atomisation.

In the embodiment of FIG. 7, the jetting orifices 33''' are inclined (e.g. up to 30° in the axial direction so as to create a relatively small amount of swirl in the overall flow whilst still retaining the beneficial effects of high turbulence caused by separation and re-attachment of the bubbly flow. Such swirl can increase the angle of the spray discharged from the apparatus. In particular this small amount of swirl is found to remove the tendency for larger drops to be formed at the center of the emerging spray, particularly at lower pressures, e.g. when the container pressure has reduced to 5 bar.

Figure 8:
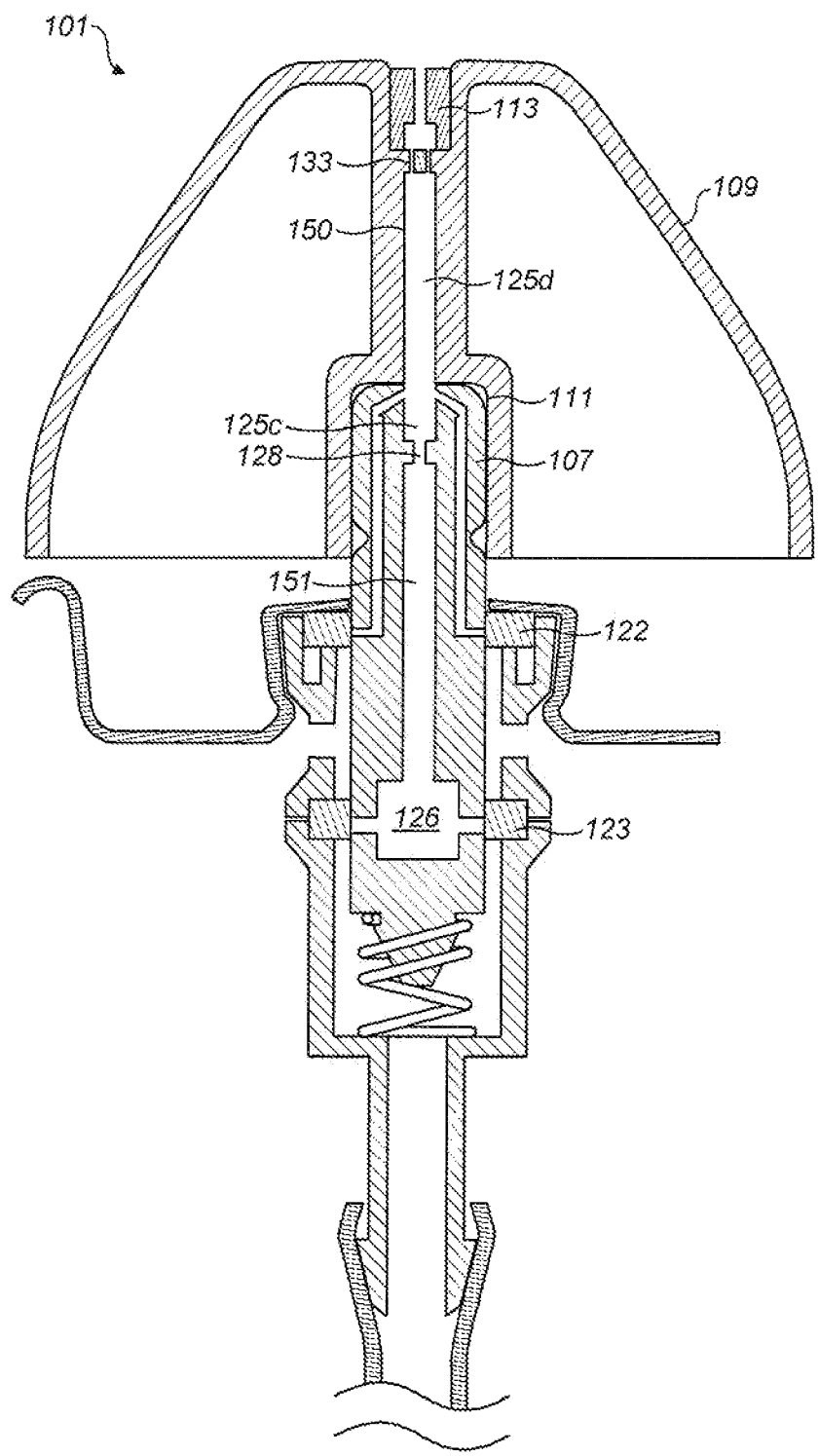

FIG. 8 of the drawings shows an embodiment of spray device 101 which operates on the same principle as the apparatus shown in, and described with reference to, FIGS. 3 and 4. Component parts of the spray device 101 which have an equivalent in the device 1 of FIGS. 3 and 4 are designated by the same reference numeral plus 100. Thus, for example, the apparatus 101 of FIG. 8 is shown as having a valve assembly 103 which is the equivalent of valve assembly 3 in the device of FIG. 3a.

The apparatus of FIG. 8 is configured to accommodate a larger actuator cap 109 than that employed in the device of FIG. 1 since the use of relatively large caps is often a commercial requirement. This is achieved in the embodiment of FIG. 8 by means of an arrangement in which the flow conduit for producing the "bubbly flow" to be supplied to the insert 113 (via the jetting orifices 133) is formed partly in the valve stem 107 and partly in the actuator cap 109. More specifically, an upstream section 125u of the flow conduit is formed in the valve stem 107 and a downstream section 125 is formed in a passageway 150 within the cap 109, this passageway 150 serving to provide communication between the lower recess 111 in the cap and the jetting orifices 133. An additional chamber 151 is formed in valve stem 107 to provide for communication between liquid feed chamber 126 and the liquid inlet 128 to flow conduit 125d. Furthermore, the transverse gas bleed inlets 29 employed in the aerosol spray device of FIG. 3a are replaced by passageways 152 which extend inwardly from the outer surface of valve stem 107 towards the chamber 151 before turning through a right-angle so as to extend parallel to chamber 151 to a position beyond passageway 128 at which they turn inwardly to communication with the upstream section 125u of the flow conduit (within valve stem 107).

With the arrangement as described, it is possible for the apparatus of FIG. 8 to accommodate a larger actuator cap 109 than is the case for the embodiment of FIG. 3a.

Figure 9:
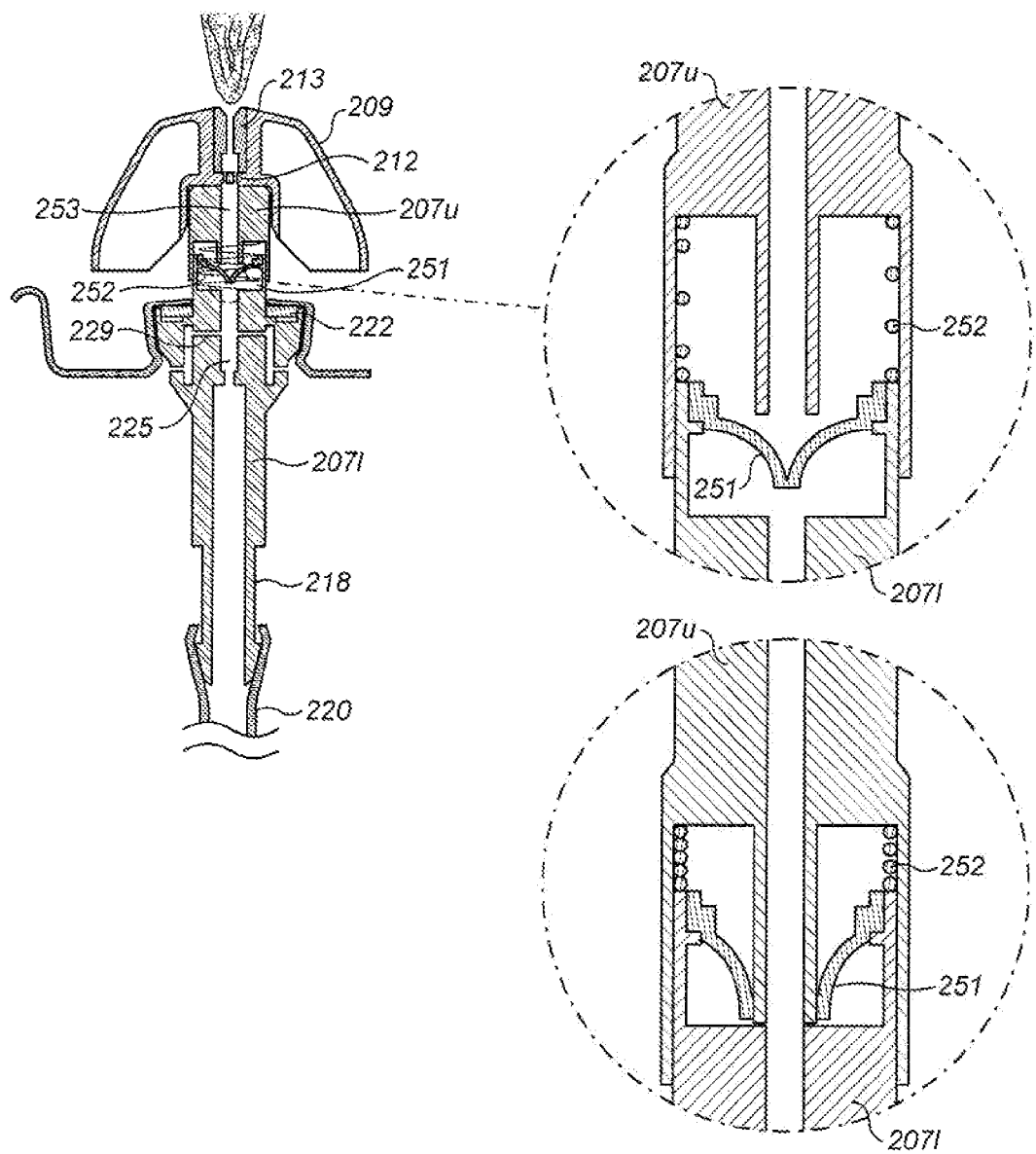

In the embodiments of the invention described so far with reference to FIGS. 3 and 8, the on/off control of gas and liquid into the flow conduit 25 is controlled by the position of passageways 28/128 and 29/129 relative to the gaskets 22/122 and 23/123. However, other arrangements are possible provided that the required bubble flow is generated in the flow conduit and passed into the insert for flow separation and re-attachment as described above. One such modified arrangement is shown in FIG. 9. Parts similar to the embodiment of FIG. 3a are identified by the same reference numeral plus two hundred (e.g. the actuator cap is designated as 209).

In the embodiment of FIG. 9, the upper end of the flow conduit 225 opens into a chamber 250 in which is accommodated a so-called "duck bill" valve 251 which is of elastomeric material and comprises a pair of flaps which open and close in the manner of the bill of a duck. More specifically, the flaps resile towards the closed position of the valve at which the flaps converge together to effect closure. The duck bill valve functions as a one-way valve which normally remains closed until an appropriate force is applied to the interior faces of the closed flaps. A suitable duck bill valve is available from Minivalve International (see www.minivalve.com). For the purposes of the present embodiment, the "duck bill" valve points downwardly. As such, the valve is held closed by the pressure within the container and is opened by depression of the actuator cap. For this purpose, the valve stem is formed in lower and upper parts 207l and 207u respectively, the former being fixed relative to the container and the latter being associated with actuator 209 for movement therewith. A coil spring 252 located between the two sections 207l and 207u of the valve stem serves to bias both the upper valve stem section 207u and the actuator 209 upwardly away from the container. A tubular projection 253 locates in upper valve stem section 207u with its upper end against (and in communication with) the jetting orifices in partition 212 and its lower end which locates in the upper, open end of the duck bill valve 251. With actuator 209 (and valve stem 207u) biased to its upper end the duck valve 251 is closed.

Additionally, valve stem 207 is modified somewhat as compared to the valve stem 7 employed in the device of FIG. 3a. More particularly:
  (i) the lower gaskets 23 and the liquid supply passageways 28 are omitted so there is no valve controlling liquid flow into the flow conduit 225;
  (ii) liquid is supplied directly to the flow conduit 225 via dip tube 220, tubular spigot 218 and chamber 226; and
  (iii) the gas bleed inlets 229 are not blocked by the seals 222 but rather are permanently in communication with the head space in the container.

To operate the aerosol spray device illustrated in FIG. 9, the actuator 209 is pressed downwardly against the bias of coil spring 252 so that its associated tubular projection 253 also moves downwardly and serves to open the "duckbill" valve 251 by moving the elastomeric flaps thereof apart as indicated in the inset to FIG. 9. Liquid is now able to flow upwardly into the flow conduit 225 where it is mixed with gas bled through the gas bleed inlets 229 to produce a "bubbly flow" in the manner described above for other embodiments of the invention.

As indicated, the embodiment of FIG. 9 does not have a separate valve for the liquid flow into the flow conduit. Therefore the liquid below the duck bill valve is all at the same pressure and equal to the pressure in the pressurised container. An advantage of this embodiment, because of this lack of a separate liquid valve and use of a "no losses" duck bill valve for turning the complete flow on and off, is that the liquid flow suffers virtually no energy losses as it flows through the valve and actuator to the insert 213. This is an advantage over the embodiment shown in FIG. 3a, although the latter has its own advantage of relatively greater simplicity.

Figure 10:
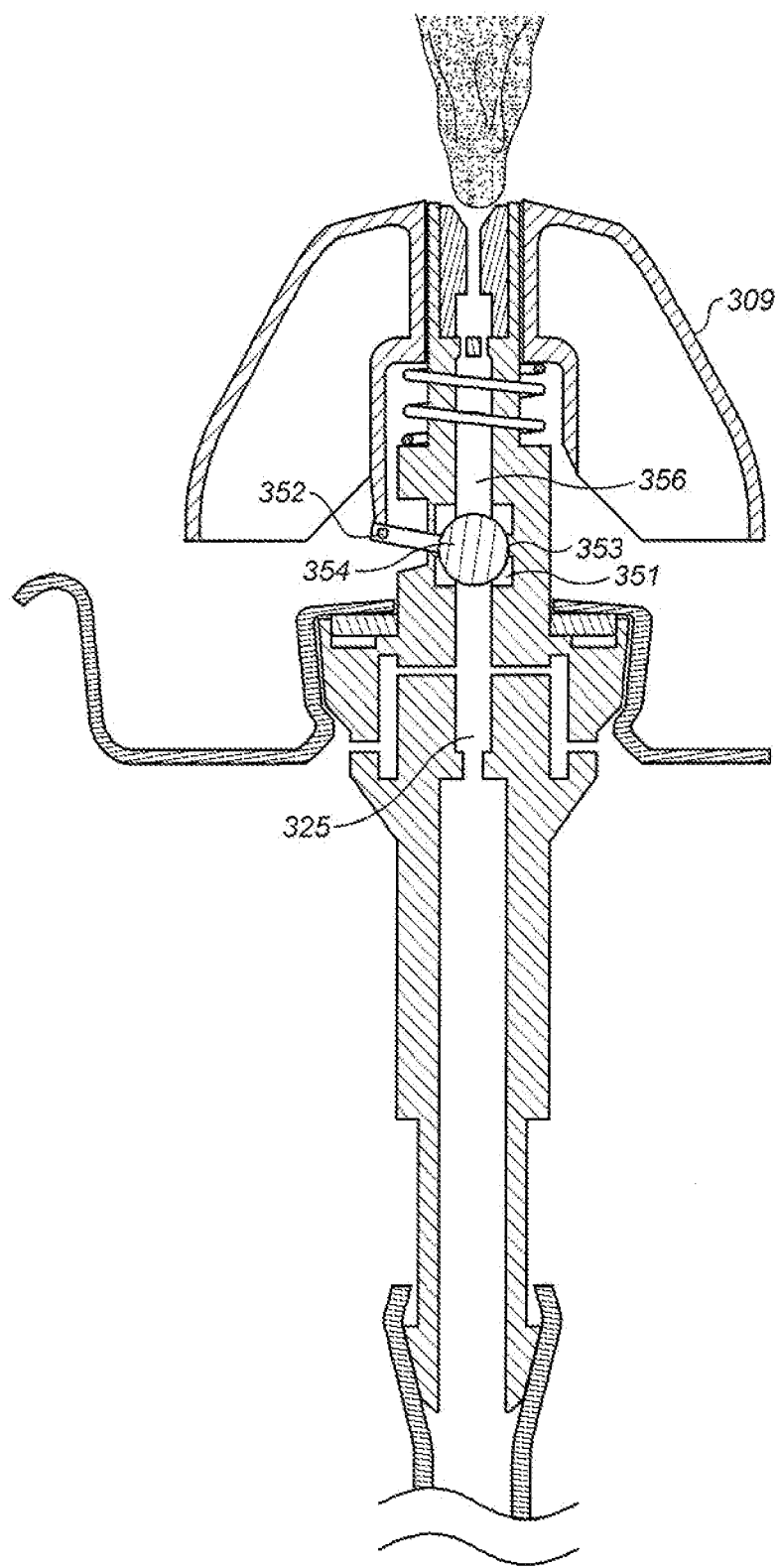

FIG. 10 shows a further embodiment of device in accordance with the invention. Component parts in the device of FIG. 10 which have a corresponding part in the embodiment of FIG. 3a or reference by the same numeral as used in the latter plus 300. The device of FIG. 10 operates on similar principles to that shown in FIG. 9 by use of a "low loss" on/off valve. In the embodiment of FIG. 10, the on/off valve is a ball valve 351 which is operated by a lever and pivot arrangement 352 by depression of the actuator cap 309. A low loss cylinder valve will also provide the same function. More particularly, the ball valve 352 has a ball 353 with a central bore 354 which, when the actuator cap is depressed, is aligned with the flow conduit 325 and a further chamber 356 in the actuator cap to allow for spray discharge.

In the embodiment of FIG. 10, the "flow conduit" can be considered to be comprised of chambers 325 and 356 when in communication via the bore 354 (of the ball valve) which itself can be considered to form part of the flow conduit.

Figure 11:
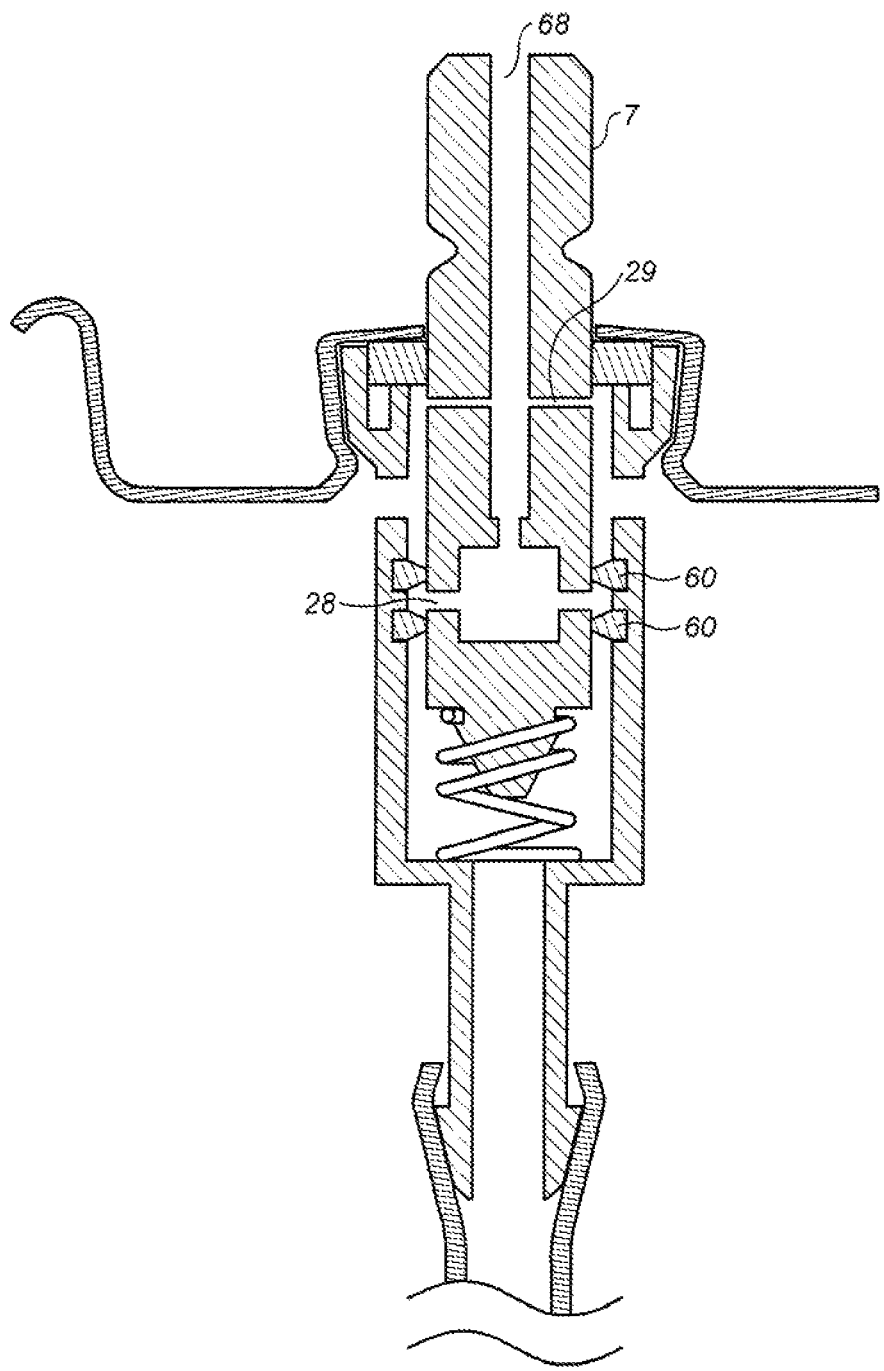
Figure 12:
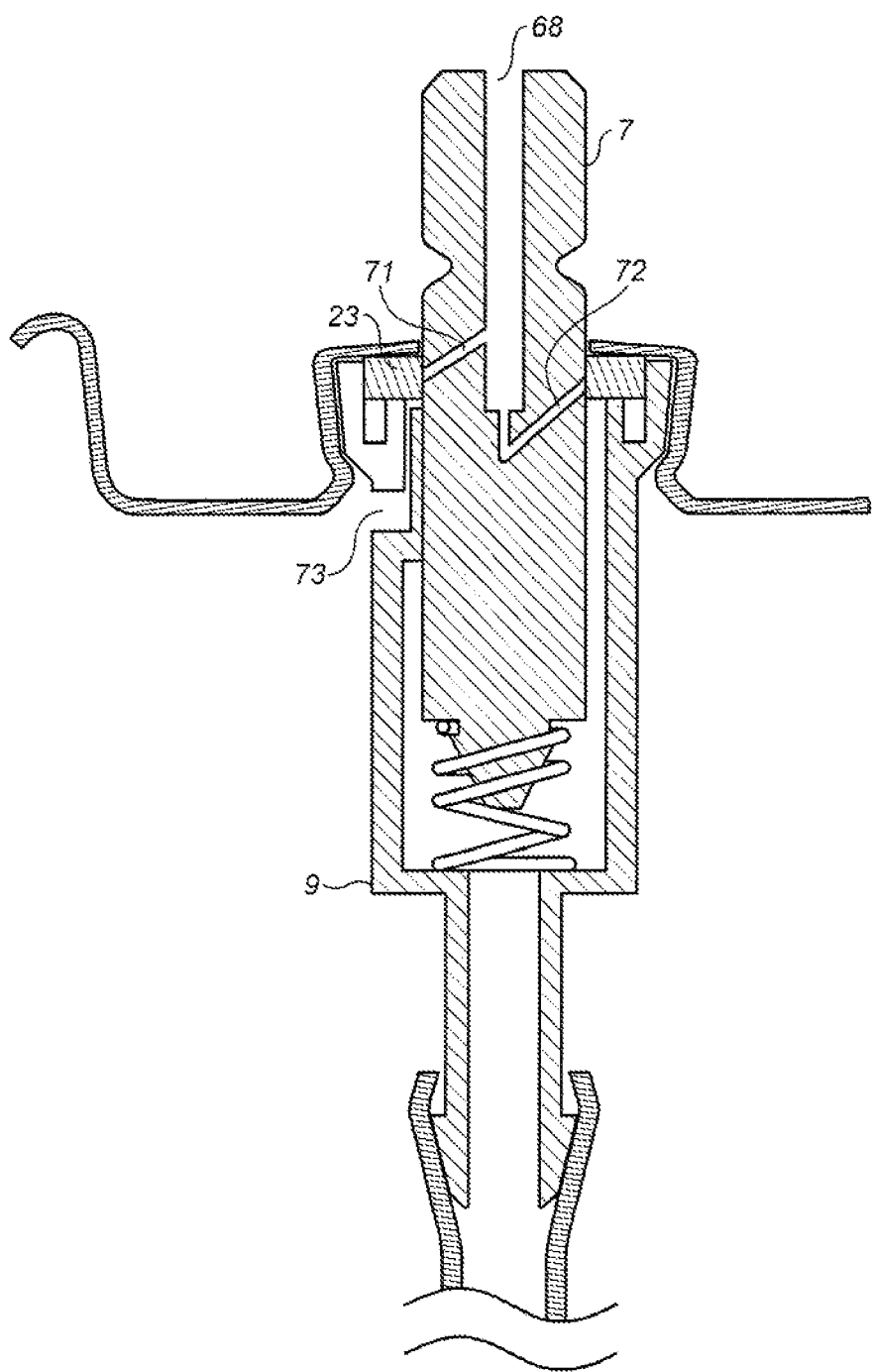

FIGS. 11 and 12 of the drawings show modified arrangements for producing the bubble-laden flow to be passed to the MBU insert.

The arrangement of FIG. 11 is similar to that of FIG. 3 save that (in the rest condition of the aerosol spray device) the passageways 28 are isolated from the liquid 5 by two O-rings 60, one above passageway 28 and one below. When valve stem 7 is depressed, the passageways 28 move past the lower O-ring 60 so as to be exposed to the high pressure liquid in the valve housing thus permitting liquid flow into the conduit. The gas bleed inlets function in exactly the same way as outlined above.

It should be noted that, although the embodiment of FIG. 11 shows a single liquid inlet passageway 27 entering coaxially into the conduit 68 at the lower end thereof, it is possible for there to be two or more liquid inlets which can be formed in the side wall of the lower part of the conduit. Furthermore although the chamber 26 (that feeds the liquid inlet 27 to the conduit 68) is shown as being fed with liquid via two passageways 28, it is possible for the valve stem to be modified such that the chamber 26 and liquid inlet 27 are omitted and the flow conduit 8 is fed directly via passageways 28 provided that they are of appropriate cross-section.

In the arrangement of FIG. 12, the lower seal 23 has been omitted and modifications made to the valve stem 7 and the housing 9 to permit the arrangement to function with the remaining, single seal 23. More specifically, the valve stem 7 incorporates for the conduit 68, a gas bleed inlet 71 and a liquid inlet 72 which, in principle, perform the same functions as passageways 29 and 28 respectively in the arrangement of FIG. 3. As shown in FIG. 12 for the rest condition of the aerosol spray device, gas bleed inlet(s) 71 is closed by seal 23 and extends upwardly away therefrom. Liquid inlet(s) 72 is of angled configuration with a short section coaxial with conduit 68 connected to a further section extending upwardly to seal 23 so as to be closed by that seal, alternatively inlet(s) 72 may enter directly into the side of the conduit 68. In other embodiments the second inlet(s) 71 may be perpendicular to the conduit 68 and in a further embodiment both the first and second inlets, 72 and 72, may enter the conduit 68 at the same orthogonal plane as the conduit 68. Additionally, a portion of the housing 9 has been modified so as to be a close sliding fit around that region of the valve stem 7 where the gas bleed inlet 71 opens at the outer surface of valve stem 7. Furthermore gas feed port 73 (equivalent to port 24 in FIG. 1) has been configured so that its outlet end feeds directly into gas bleed inlet 71 when valve stem 7 is depressed. These arrangements avoid leakage of gas from the headspace of the container into the liquid inlet 72 or liquid leaking into the gas inlet 71. Whilst it is desirable to avoid such leakages as much as possible they are not a major problem because the gas and liquid are at essentially the same pressure in the container 2.

The embodiment of FIG. 12 has various advantages. In particular, it employs fewer parts and thus reduces material, manufacturing and assembly costs. Additionally it may readily be produced in dimensions well suited to manufacture with the same overall dimensions as conventional liquefied gas propellant aerosol valves.

It should be appreciated that various modifications may be made to the illustrated embodiments. Thus, for example, the embodiment of spray device shown in FIG. 11 may have two or more of each of the gas bleed inlet and liquid feed inlet. More generally, embodiments of spray device in accordance with the invention may have 1 to 6 gas bleed inlets, preferably with a total cross-section equivalent to a single inlet of 0.15-0.7 mm diameter. Similarly there may be 1 to 6 liquid inlets with a total cross-section equivalent to a single inlet of 0.15-0.7 mm diameter.

Furthermore although some embodiments are illustrated with four swirl channels, it is possible more generally to use inserts with 1 to 8 such channels.

The invention claimed is:

1. A spray discharge assembly for an aerosol spray device comprising a pressurized container holding a liquid to be discharged from the device by a gaseous propellant that is a gas at a temperature of 25° C. and a pressure of at least 50 bar, the spray discharge assembly adapted to be inserted in a fluid flow path between fluid in the container and a nozzle, the spray discharge assembly comprising:
   (i) an approach channel having at least one inlet and an outlet,
   (ii) a flow conduit, located upstream of said approach channel in a direction of liquid discharge from the nozzle, for supplying fluid to be discharged to the approach channel,
   (iii) at least one jetting orifice through which fluid from the conduit passes and issues as a jet into the approach channel through the inlet thereof, the jetting orifice being located between the flow conduit and the approach channel, and
   (iv) a discharge orifice into which fluid from the approach channel passes via the outlet thereof to issue as a spray from the nozzle, the discharge orifice being located downstream of the approach channel,
   wherein the flow conduit has at least one liquid inlet and at least one gas inlet configured to generate a bubble-laden flow in the flow conduit;
   wherein the outlet of the approach channel is surrounded by a sharp edge and the jetting orifice is configured for directing the jet against said edge;
   wherein the discharge orifice comprises a straight-sided cylindrical bore with a diameter defined by the outlet of the approach channel;
   wherein the length of the straight-sided cylindrical bore is 4 to 15 times its diameter;
   wherein the jetting orifice, sharp edge and discharge orifice are positioned to enable separation of the bubble-laden flow from an interior surface of the straight-sided cylindrical bore over an upstream region thereof; and
   wherein the length of the straight-sided cylindrical bore is such that reattachment of the bubble-laden flow to the interior surface of the straight-sided cylindrical bore at a downstream region thereof is enabled.

2. An assembly according to claim 1, wherein the approach channel is cylindrical and has a diameter of 0.5 to 3 mm and an axial length of 0.2 to 2 mm.

3. An assembly according to claim 2, wherein the approach channel has a diameter equal to its axial length.

4. An assembly according to claim 3, wherein the diameter and the axial length of the approach channel are both about 1 mm.

5. An assembly according to claim 1, wherein the discharge orifice is cylindrical and has a uniform diameter of 0.1 to 0.75 mm and a length from 4 to 12 times its diameter.

6. An assembly according to claim 5, wherein the discharge orifice has a diameter of 0.20 to 0.50 mm.

7. An assembly according to claim 6, wherein the diameter of the discharge orifice is about 0.3 mm.

8. An assembly according to claim 1, comprising a plurality of said jetting orifices.

9. An assembly according to claim 8, comprising three to six of said jetting orifices.

10. An assembly according to claim 9, comprising four of said jetting orifices.

11. An assembly according to claim 1, wherein the at least one jetting orifice has a diameter of 0.1 to 0.5 mm.

12. An assembly according to claim 11, wherein the jetting orifices have a diameter of 0.25 mm.

13. An assembly according to claim 1, wherein said sharp edge presents a reflex angle of at least 270°.

14. An assembly according to claim 13, wherein said sharp edge presents a reflex angle of 270° to 330°.

15. An assembly according to claim 14, wherein said sharp edge presents an angle of about 270° to the interior of the approach channel.

16. An assembly according to claim 1, wherein said sharp edge is provided at the apex of a conical projection within which the discharge orifice is at least partly formed.

17. An assembly according to claim 1, wherein a radius of curvature at the sharp edge is less than 100 microns.

18. An assembly according to claim 17, wherein the radius of curvature at the sharp edge is less than 25 microns.

19. An assembly according to claim 1, wherein the discharge orifice is contiguous with, and defined by, the diameter of the outlet of the approach channel.

\* \* \* \* \*